United States Patent [19]

Klausz

[11] 4,345,157
[45] Aug. 17, 1982

[54] PROCESS FOR USE OF AN X-RAY TOMO-SCANNER MAKING IT POSSIBLE TO PERFORM CINEDENSIGRAPHY AND CORRESPONDING ADAPTATION OF TOMO-SCANNER

[75] Inventor: Remy Klausz, Paris, France

[73] Assignee: Thomson-CSF, Paris, France

[21] Appl. No.: 168,105

[22] Filed: Jul. 14, 1980

[30] Foreign Application Priority Data

Jul. 17, 1979 [FR] France ................................. 79 18463

[51] Int. Cl.³ .............................................. A61B 6/00
[52] U.S. Cl. ...................................... 378/19; 128/653
[58] Field of Search ...................... 250/445 T; 128/653

[56] References Cited
U.S. PATENT DOCUMENTS 3,952,201  4/1976  Hounsfield ...................... 250/445 T
4,182,311  1/1980  Seppi et al. ...................... 250/445 T Primary Examiner—Alfred E. Smith
Assistant Examiner—T. N. Grigsby
Attorney, Agent, or Firm—Oblon, Fisher, Spivak, McClelland & Maier

[57] ABSTRACT

The invention relates to a novel process for the use of a transverse axial tomo-scanner in such a way that it can be used for carrying out cinedensigraphy.

Instead of measuring the different projections of the cross-section during examination as a function of the different angular positions of the radiation absorbing device, the same projection (i.e. with a fixed device in the plane of the section) is measured at different times constituting a sampling of the phenomenon to be observed.

It is thus possible to visually display the evolution in time of cyclic or non-cyclic phenomena by using equipment which is not, a priori, intended for this purpose.

11 Claims, 6 Drawing Figures

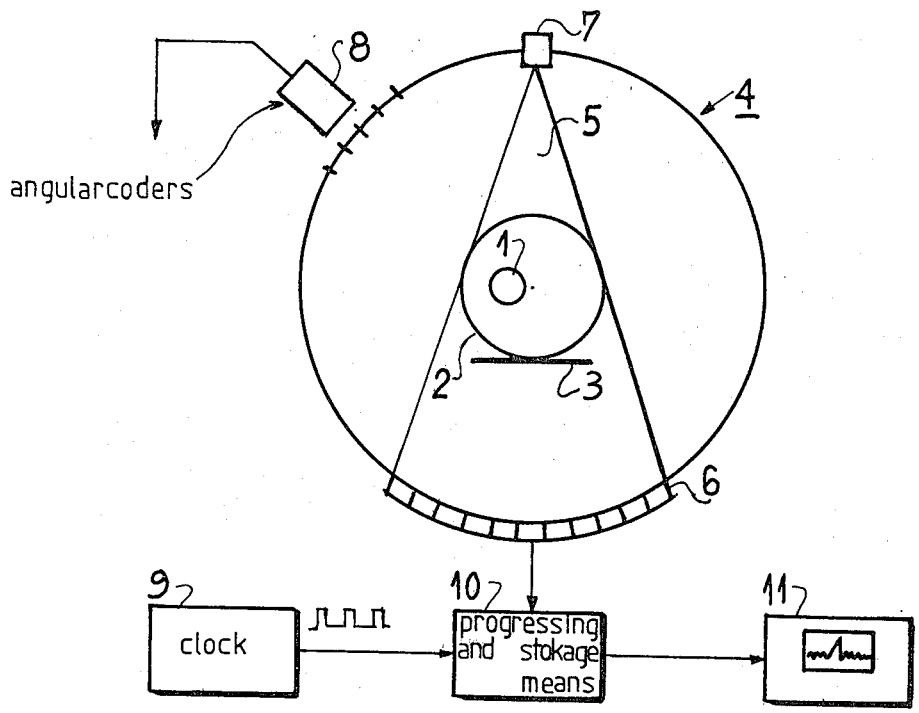
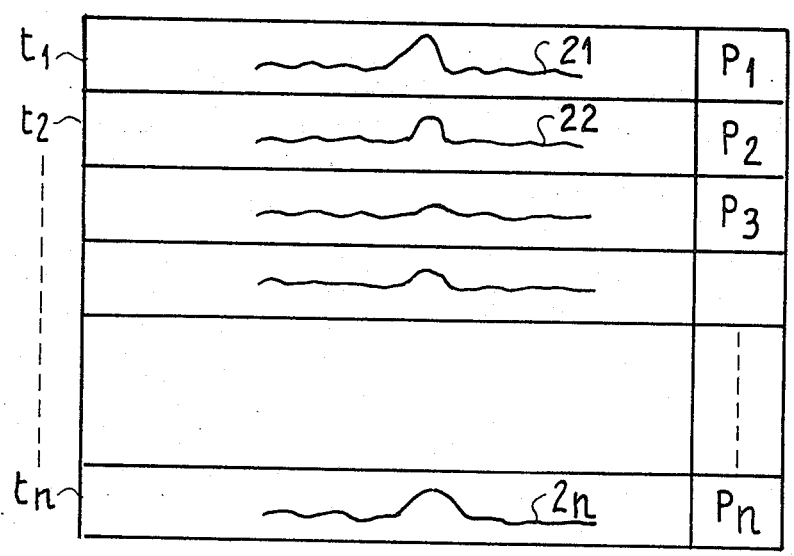

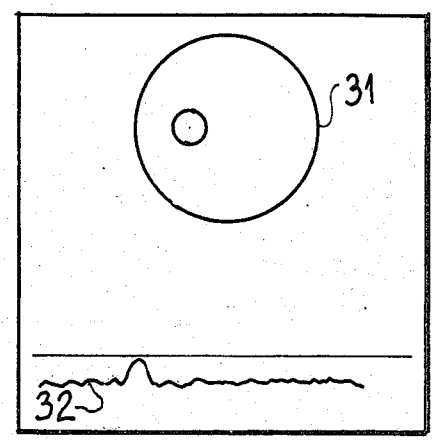
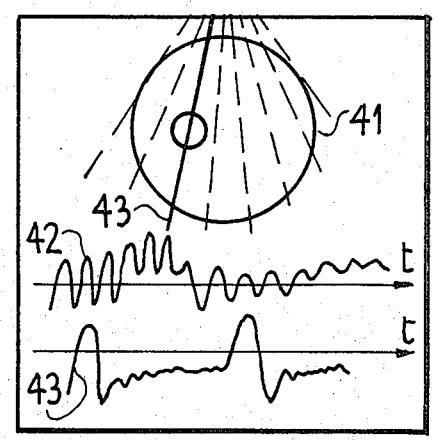
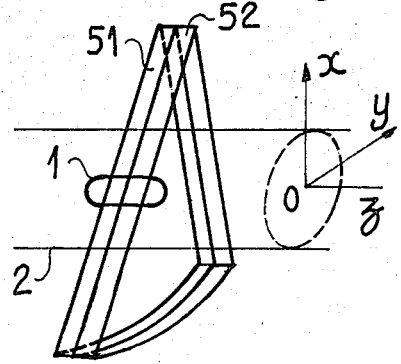
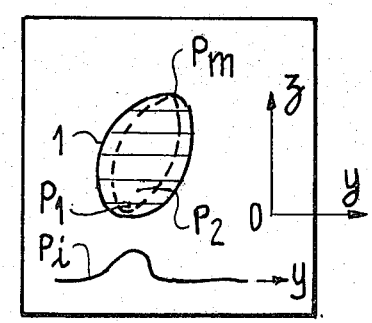

PROCESS FOR USE OF AN X-RAY TOMO-SCANNER MAKING IT POSSIBLE TO PERFORM CINEDENSIGRAPHY AND CORRESPONDING ADAPTATION OF TOMO-SCANNER

BACKGROUND OF THE INVENTION

The present invention relates to a novel process for the use of an X-ray tomo-scanner which, by certain adaptations, makes it possible to use it for carrying out cinedensigraphy, whilst sill maintaining a normal operating mode. It also relates to a tomo-scanner suitable for use in cinedensigraphy in this way.

Cinedensigraphy techniques have been known for a long time and were developed in France by Mr Henri-Maurice MARCHAL and are described for example in Volume 1 of the work entitled "Traité de radiodiagnostic" by J. BUTREIX, V. BISMUTH and M. LAVAL-JEANTET, published by Masson et Cie, pp.372ff.

The hitherto known method for obtaining a cinedensigraphic recording comprised irradiating the area of the patient to be observed by an X-ray beam, collecting the transmitted X-rays on a detection cell, converting them into an electrical signal and recording the amplitude of said signal as a function of time.

This method was mainly used for defining and locating abnormalities in the lungs. Thus, an abnormality such as a tumour modifies the movements in the lung in its breathing function and affects the vascular system. If it is possible to observe the amplitude of the movements in the different areas of the lungs it is possible to define the areas in which these movements are abnormally small and correspond to an abnormality. It is also of interest to be able to observe how, over a period of time, the density of the different zones observed behave, even if there are no deformations of organs.

In this hitherto known method the collected electrical signal, which varies in time, corresponds to an integration of the information over the entire area considered by the detection cell. This integration takes place not only on the thickness of the subject traversed by the X-ray beam, but also on the surface of the subject corresponding to the cross-section of the irradiating beam.

The fact that it is necessary to have specialised equipment has meant that this cinedensigraphy method has stayed at the laboratory stage, in spite of the interesting results which it can provide on the behaviour over a period of time of organs exposed to X-rays.

In addition, tomo-scanning or transverse axial tomography techniques are known. Unlike cinedensigraphy which attempts to obtain information on attenuation variations over a small area as a function of time, tomo-scanning makes it possible to reconstitute the linear attenuation coefficient value at any point of a section or cross-section and reconstruct the image of this section. However, it only gives good results if the object examined is strictly identical to itself at all times during scanning. Unless this complete absence of variation in time of the shape and/or density of the examined object is ensured, the reconstituted image is imprecise or blurred.

BRIEF SUMMARY OF THE INVENTION

The present invention relates to a novel process for using a tomo-scanner permitting the use thereof for carrying out cinedensigraphy, whilst still permitting it to be used in the normal manner for transverse axial tomography. Thus, a few inexpensive modifications made to a conventional tomo-scanner makes it possible for a medical examination centre owning such an apparatus to operate it according to the process of the invention and carry out cinedensigraphy examinations with no need for acquiring special equipment for this purpose.

It is very important to note that these modifications do not stop the apparatus from being used for normal tomo-scanning and a change for one operating procedure to the other merely involves a switching process. As can be gathered from the following description, the combination of the two techniques is very advantageous.

The present invention relates to a novel process for the use of an X-ray tomo-scanner making it possible to obtain, in accordance with the cinedensigraphy technique, information characteristic of the evolution in time of the shape and/or density of parts of a subject irradiated by X-rays, wherein it comprises subjecting each section to be examined to X-rays supplied by the source of the measuring device of the tomo-scanner and measuring the radiation transmitted to the detection means facing the said source, said measuring device supplying N signals corresponding to the absorption undergone respectively by N elementary beams whilst passing through the section and defining a projection of said section at the time of this first measurement, N being an integer equal to or above 1; repeating this measurement a number of times so as to obtain the values taken by the N signals for the same projection, i.e. with a constant incidence of the X-rays relative to the section to be examined, at different times, thus bringing about a sampling of said projection in time; processing and storing the thus obtained sequences of N signals; and visually displaying the amplitude of the sequences of N signals obtained as a function of time for 1 or more given elementary beams and/or at constant time for the different elementary beams.

BRIEF DESCRIPTION OF THE DRAWINGS

The invention is described in greater detail hereinafter relative to non-limitative embodiments and with reference to the attached drawings, wherein show:

FIG. 1 a very diagrammatical view of the essential elements of a tomo-scanner construction used in accordance with the process of the invention.

FIGS. 2, 3 and 4 examples of the storage and visual display modes of the data processed by the apparatus of FIG. 1.

FIGS. 5a and 5b very diagrammatic views of a particular utilization mode of the apparatus according to the invention.

DETAILED DESCRIPTION OF THE PREFERRED EMBODIMENTS

It should be noted that the tomo-scanner more specifically used here has an X-ray absorption measuring device with a fan-like beam and with N detectors. However, it is also possible to use other types of tomo-scanners. It can for example, be a tomo-scanner with a single detector displaced in translation in the plane of the section to be observed in such a way that the N successive positions taken by the source-detector assembly during the time $\Delta t$ for processing N signals give the N elementary beams producing said N signals. In such a case, the processing time of N signals corresponding to a sampling operation is not negligible. It is for this reason that versions with N detectors operating simultaneously are preferable for performing the process of the invention. However, such a tomo-scanner with a single detector can be used in an interesting manner if the time Δt for processing the N signals is sufficiently short compared with the shape and/or density variation rate of the organs to be observed. It is also possible to use this type of apparatus when there is only interest in a very limited area of the body, the source-detector assembly then occupying a fixed position in such a way that the thin X-ray beam traverses said area and the number N of signals is then reduced to 1.

It is also possible to use a tomo-scanner with a single source and a number of detectors operating normally in translation/rotation when it is a question of carrying out transverse axial tomography. The N signals can be processed by translating the source-detector assembly. If no great analytical precision of the projection examined in cinedensigraphy is required, there need only be a single position.

Finally, it can be tomo-scanner with one source and numerous (>N) detectors arranged in a ring around the source. In this case, only certain of the detectors of the ring are used for processing the N signals. When using one of the three types of tomo-scanners, with a fan-like beam, it is possible to use for cinedensigraphy only part of the detectors struck by the X-ray beam.

FIG. 1 very diagrammatically shows the essential elements of a tomo-scanner used in accordance with the process of the invention for obtaining cinedensigraphy data. It makes it possible to observe the evolution of shape and/or density of organs in time and for example the deformations of the heart 1 of a patient 2 placed on a support 3.

This apparatus comprises an X-ray absorption measuring device 4, which is that of a fan-like beam tomo-scanner 5 and with N detectors 6 arranged in a circular arc facing an X-ray source 7. This device is conventionally fixed to a not shown stand. The N detectors 6 collecting the X-ray beam after it has passed through the section of the patient 2 to be observed determine N elementary beams, constituting in the present case N juxtaposed fractions of beam 5 and supply the N signals corresponding to the processing and storage means 10 of the tomo-scanner.

In the conventional use of a tomo-scanner the measuring device 7, 6 rotates around the patient over at least half a revolution. Each angular position, determined for example by means of optical coders such as 8, leads to the processing of N values processed and stored at 10. The combination of all the groups of N values, i.e. all the projections by given algorithms makes it possible to reconstruct point by point the image of the section examined.

However, in the process of the invention, once the orientation of the measuring device 7, 6 has been chosen in the plane of the section to be examined, said device remains fixed so as to be able to take the various samples (group of N signals) in the time of one and the same projection. For this purpose, the means for defining the angular position (e.g. sensors 8) no longer control the measurement connection. Their action is replaced by that of the pulse generator or clock 9 controlling the processing, treatment and storage at 10 of groups of N signals at the rhythm of said clock frequency.

The frequency of these pulses which determines the sampling times of the phenomenon to be observed is either constant, or regulatable by the operator as a function of the deformation rate of the organ under observation. It can even be made dependent on a biological phenomenon, such as the electrical activity of the heart (electrocardiogram or ECG). In all cases, it must be compatible with the signals coming from angular coders (such as 8) in the normal usage of the tomo-scanner, because in the process of the invention the clock signal simulates the signals coming from these coders.

It should be noted that it is possible to utilise the possibility of measuring device 7,6 of rotating around the patient in order to easily select the best incidence for observing the phenomenon to be monitored (deformation of organs, density variations). This selection of the best incidence prevents parts of the subject other than those being investigated from supplying an interfering signal superimposed on that of the part which is to be observed. Thus, for cinedensigraphic observations, it is necessary to choose a predetermined projection among the numerous projections of transverse axis tomography by rotating the transmitter-receiver assembly in the desired angular direction. To select this direction, it is advantageously possible to use information supplied by a previously obtained tomo-scanning image of the corresponding cross-section. In the case of using a tomo-scanner with detectors in a fixed ring it is carried out by rotating the single X-ray source in the desired direction and collecting the corresponding data on the N facing detectors.

Thus, to carry out cinedensigraphy with a tomo-scanner according to the process described hereinbefore, it is merely necessary to add thereto a clock 9 controlling, in place of the angular detection means 8, the taking of data by the processing and storage means, not using the image reconstruction algorithms and using visual display means 11 in the manner to be described hereinafter. To pass from one operating mode to another, it is merely necessary to use switching operations which fall within the non-inventive scope of the Expert.

The sequences of N data obtained in this way correspond to a sampling in space (along N elementary beams defined by the N detectors) and in time (at the clock rhythm) of the different states of the section observed and for example the heart.

In order to obtain information on the sampling times, it may be of interest to record simultaneously with the taking of the data, one or more reference signals (such as the clock signal or a signal soming from a biological sensor).

The thus processed data from the sequences of N signals obtained for each sampling operation can be displayed on visual display means 11 following possible conventional calculations, using logarithms, bringing to scale, adjusting relative to a reference, etc. Instead of being used in the usual tomo-scanning reconstruction calculations, the N data corresponding to each sampling instant defining a projection are placed in a line of the file of the store which is to contain the reconstructed image. They then follow the normal path of a reconstituted tomo-scanning image and are transmitted to the storage and visual display means. The attenuation curves displaying said data are easy to plot by means of diagnostic functions on image equipping a tomo-scanner display device, such as the density profile curve.

In the case where each line of the store file contains the N data of a projection, a curve along a line represents the values of the projection at a given time, i.e. the values of N data obtained during the sampling operation. A curve along a column represents the values at a point of the projection as a function of time, i.e. the values of one of the N signals obtained from one of the N detectors.

FIG. 2 diagrammatically represents such a digital file organisation where curves 21, 22 ... 2n each represent a projection at a given sampling time $t_1, t_2 \ldots t_n$.

If the value of one or more biological parameters symbolized by the value $P_1, P_2 \ldots P_n$ has been recorded in each line, a column curve containing these values will reconstitute the variation line of this parameter as a function of time in the same way as a recorder or oscilloscope. This parameter can, for example, be the electrical activity of the heart, said curve supplying the electrocardiogram (ECG). It should be noted that this possibility can be applied to the standard tomo-scanning images by adding one or more special channels for the acquisition and digitization of biological parameters, whose characteristics are compatible with those in use on specialized recorders, the sampling being defined by the angular sampling and the value of said parameter being placed, for example, in the first or last column of the calculated image.

On the basis of a thus constituted file, it is possible to carry out several display combinations and types, certain of these being shown hereinafter.

With respect to the image of the content of the file illustrated in FIG. 2, it is possible to display some of the N curves 21, 22 ... 2n corresponding to selected sampling times, for example using the value of the supplementary parameter at said times. The deformations in time at each point of the projection are visible on a vertical line.

As illustrated in FIG. 3, it is possible to combine a conventional tomo-scanning image 31 of the examined section and curve 32 at a given time of the projection in accordance with the direction, or selected mean direction, of said section obtained according to the invention. It is then possible by successively representing at 32 the different curves in time of said projection, to "see it move". The latter possibility can also be used alone, without being associated with image 31.

As is diagrammatically shown in FIG. 4, it is possible to associate with the tomo-scanning image 41 the time curve 42 at anyone of the points of the projection (one of the N detectors). The point of the projection where it is desired to see the variations in time can be selected by using the means existing on said display devices of tomo-scanners. Thus, for example, it is possible to display on image 41 the straight line 43 corresponding to the point of the projection which it is desired to observe, said line being selected from among N possible lines by a button on the visual display console which is available to the operator.

It is often of interest to compare the evolution in time 42 of said point with the variation in time of another biological parameter such as the ECG. It is easily possible to display beneath curve 42 the curve 43 which represents said parameter by bringing about time correspondence on the two curves.

Thus, in addition to the fact that it does not require special equipment because it is merely necessary to adapt a tomo-scanner as described hereinbefore, the presently described cinedensigraphy process has a great flexibility of use, because it makes it possible to represent the variations of an organ as a function of space (FIGS. 2 and 3) and/or as a function of time (FIG. 4).

Another utilization mode of the apparatus of the invention can also be of interest and this is illustrated in FIG. 5.

The cinedensigraphy measurements are performed as hereinbefore with a fixed stand in the plane of the section to be observed. However, the operation is performed several times for different relative positions of the stand along the longitudinal axis of the subject. This is diagrammatically shown in FIG. 5a where it is possible to see two successive positions 51 and 52 of the fan-like beam displaced along the longitudinal axis Oz of the subject.

Several series of measurements are made in this way, the stand remaining fixed relative to the Ox and Oy axes which define the parallel planes of the sections of the subject and moving along the Oz axis in relative manner with respect to the subject 2.

It should be noted that this utilization method, used here in cinedensigraphy, is similar to the use of a tomoscanner in radiography, where it is used by numerous designers and is described for example in Siemens French Patent Application No. 77.04724 published under No. 2,345,983. In the radiography mode, the subject is moved parallel to Oz, data being taken with fixed incidence as in the present case. The resulting image is equivalent to a conventional X-ray picture, i.e. the heart 1 is represented in the manner shown in FIG. 5b by projection on a plane (plane Oy, Oz). This image 1 of FIG. 5b is constituted by the juxtapositioning of the different projections $P_1, P_2 \ldots P_n$ obtained during the m successive positions of the subject along Oz. The curve of one of these projections is shown at $P_i$ in FIG. 5b.

The cinedensigraphic measurements obtained as previously described combined with this longitudinal displacement of the stand relative to the subject make it possible to see the examined organ "move" and specifically the heart 1 "beat". To this end, it is merely necessary to carry out for each relative position of the subject with respect to the stand, a series of projections as a function of time during a cycle of the phenomenon under observation, in this case the heartbeat.

Instead of carrying out all N projections of the same position (51, 52 ...) in a consecutive manner before changing position, it is also possible to successively perform one projection per position over a short total time with respect to the variations of the observed phenomenon. After a short delay such as series of measurements are recommenced for as many times as is necessary to have samples. It is then only necessary for the phenomenon to be cyclic. Thus, in all cases, there are N curves of the same projection taken at different sampling times either consecutively, or successively between the different positions for each individual position.

It is then merely necessary to successively switch to the visually displayed image (FIG. 5b) the projections $P_1, P_2 \ldots P_m$ corresponding to the sampling times in order to see the organ "move" and more particularly see the heart "beat".

This method of using the apparatus according to the invention makes it possible to obtain a result close to the results given by very different means in the kymography method.

What is claimed is:

1. An X-ray tomo-scanner comprising:
   a radiation absorption measuring device supplying N signals corresponding to the absorption undergone respectively by N elementary beams while passing through a section to be examined and defining a projection of said section at the time of a first measurement, N being an integer equal to or greater than 1;

means for processing and storing the obtained sequences of N signals;

a clock means for controlling each measurement operation leading to the N signals with the sampling occurring at the rhythm of the output of the clock to indicate different states of said section observed with said clock signals being supplied whenever the tomo-scanner is used in cinedensigraphy to the processing and storage means in place of the signals, which, when used in tomo-scanning, indicate the angular position of the measuring device; and visual display means for displaying the amplitude of the sequences of N signals obtained as a function of time for one or more given elementary beams and/or at a constant time for the different elementary beams.

2. A tomo-scanner according to claim 1, wherein it comprises means for switching from the cinedensigraphy mode to the tomo-scanning mode and vice versa in such a way that both examination modes can be performed.

3. A tomo-scanner according to claims 1 or 2, wherein the frequency of the clock signals is constant.

4. A tomo-scanner according to claims 1 or 2, wherein the frequency of the clock signals is regulatable by the operator.

5. A tomo-scanner according to claims 1 or 2, wherein the clock signals are dependent on a biological phenomenon of the patient under observation.

6. A tomo-scanner according to claim 1, wherein its measuring device incorporates a source supplying a narrow beam and a single detector.

7. A tomo-scanner according to claim 1, wherein its measuring device incorporates a source supplying a fan-like beam, the N elementary beam giving rise to N signals characterizing a projection being defined by N detectors receeiving the fan-like beam.

8. A novel process for the use of an X-ray tomo-scanner making it possible to obtain, in accordance with the cinedensigraphy technique, information characteristic of the evolution in time of the shape and/or density of parts of a subject irradiated by X-rays, wherein it comprises subjecting each section to be examined to X-rays supplied by the source of the measuring device of the tomo-scanner and measuring the radiation transmitted to the detection means facing the said source, said measuring device supplying N signals corresponding to the absorption undergone respectively by N elementary beams whilst passing through the section and defining a projection of said section at the time of this first measurement, N being an integer equal to or above 1; repeating this measurement a number of times so as to obtain the values taken by the N signals for the same projection, i.e. with a constant incidence of the X-rays relative to the section to be examined, at different times, thus bringing about a sampling of said projection in time; processing and storing the thus obtained sequences of N signals; and visually displaying the amplitude of the sequences of N signals obtained as a function of time for one or more given elementary beams and/or at constant time for the different elementary beams.

9. A process according to claim 8, wherein the sequences of N signals are processed and stored in tomo-scanner processing and storage means.

10. A process according to claim 8, wherein the sequences of N signals are visually displayed on tomo-scanner visual display means.

11. A utilization process in cinedensigraphy of a tomo-scanner according to any one of the claims 8 to 10, wherein it also comprises performing a relative displacement of the measuring device along the longitudinal axis of the patient being examined, i.e. perpendicular to the observed cross-section, a series of cinedensigraphic measurements being performed for a certain number of positions of said device along ths said axis.

* * * * *